(12) United States Patent
McAfee

(10) Patent No.: US 7,354,453 B2
(45) Date of Patent: Apr. 8, 2008

(54) NUCLEUS REPLACEMENT SECURING DEVICE AND METHOD

(75) Inventor: Paul McAfee, Sparks, MD (US)

(73) Assignee: Innovative Spinal Technologies, Mansfield, MA (US)

( * ) Notice: Subject to any disclaimer, the term of this patent is extended or adjusted under 35 U.S.C. 154(b) by 0 days.

(21) Appl. No.: 11/473,302

(22) Filed: Jun. 22, 2006

(65) Prior Publication Data

US 2006/0271198 A1 Nov. 30, 2006

(51) Int. Cl.
*A61F 2/44* (2006.01)

(52) U.S. Cl. .................... 623/17.16; 623/17.11; 606/61

(58) Field of Classification Search ............. 623/17.11, 623/17.12, 17.15, 17.16; 606/61
See application file for complete search history.

(56) References Cited

U.S. PATENT DOCUMENTS

| | | | |
|---|---|---|---|
| 4,790,303 A | 12/1988 | Steffee | |
| 6,093,205 A | 7/2000 | McLeod et al. | |
| 6,277,120 B1 | 8/2001 | Lawson | |
| 6,368,326 B1 | 4/2002 | Dakin et al. | |
| 6,371,990 B1 | 4/2002 | Ferree | |
| 6,551,320 B2 | 4/2003 | Lieberman | |
| 6,592,625 B2 | 7/2003 | Cauthen | |
| 6,602,291 B1 | 8/2003 | Ray | |
| 6,610,064 B1 | 8/2003 | Goble et al. | |
| 6,645,211 B2 | 11/2003 | Magana | |
| 6,923,811 B1 | 8/2005 | Carl et al. | |
| 2003/0014118 A1 | 1/2003 | Lambrecht et al. | |
| 2004/0030392 A1 | 2/2004 | Lambrecht et al. | |
| 2004/0039392 A1 | 2/2004 | Trieu | |
| 2005/0149197 A1 | 7/2005 | Cauthen | |

FOREIGN PATENT DOCUMENTS

WO WO 02/058599 8/2002

OTHER PUBLICATIONS

International Search Report and Written Opinion issued for PCT/US04/41439 dated Oct. 14, 2005.

*Primary Examiner*—Corrine McDermott
*Assistant Examiner*—Javier G. Blanco
(74) *Attorney, Agent, or Firm*—Carr LLP

(57) ABSTRACT

There is disclosed systems and methods for spinal nucleus replacement by constructing channels through vertebral segments on either side of an area into which the spinal nucleus is to be positioned, the channels running from a channel end outside of the area to a channel end abutting the area. One end of a suture is inserted into the outside channel end of a first one of the channels and passed through the first channel and into the area and out of the area through the second channel until it emerges from the second channel. The suture is then used to pull the nucleus into the area.

3 Claims, 3 Drawing Sheets

NUCLEUS REPLACEMENT SECURING DEVICE AND METHOD

RELATED APPLICATIONS

This application is a divisional of U.S. patent application Ser. No. 11/007,648 filed Dec. 7, 2004 now abandoned and entitled "Nucleus Replacement Securing Device and Method", which claims priority to U.S. Provisional Patent Application Ser. No. 60/527,855 entitled "Nucleus Replacement Securing Device and Method", filed Dec. 8, 2003, the disclosure of which is hereby incorporated herein by reference.

TECHNICAL FIELD

This invention relates to securing of a nucleus replacement and more specifically, to assistance in placing, stabilizing, and securing of a nucleus replacement in the disc space between two adjacent vertebrae from a posterior, posterolateral, or lateral approach.

BACKGROUND OF THE INVENTION

Spinal discs are the primary mechanical cushion for the vertebral column and permit controlled motion between the vertebral segments. Over time, these discs have a tendency to loose water which in turn reduces their cushioning ability. Along with a reduced hydraulic nature, the disc loses its ability to maintain disc height and bear loads resulting in a cascade of degenerative effects. As this degenerative process continues, a disc herniation involving bulging or expelling of disc material can occur leading to pain to the back and lower extremities. When this occurs, it is necessary to remove the herniated disc and reestablish disc height, ultimately in an effort to reduce or eliminate pain.

When the pain generating disc is removed, the disc space will collapse resulting in instability and further trauma to surrounding tissue and ensuing pain. Current treatments include installing a bone brace, cage, or other load bearing means often along with bone growth stimulators in an effort to cause fusion of the segment and thus alleviate the pain. This process is, however, believed to place undo stress on other vertebral levels as they compensate for the lack of motion, in turn potentially leading to premature failure of those other discs as well.

An improved solution includes replacing the removed internal portion of the disc, or the nucleus, with a nucleus prosthesis to act as the load bearing and motion stabilizing feature in an effort to restore natural spine biomechanics.

Devices such as these are outlined in U.S. Pat. No. 6,602,291 wherein the nucleus replacement is inserted into the disc space is a reduced size state, and then is hydrolyzed (or otherwise expanded) to fill the gap. Current methods and concepts have undergone human clinical trials to little success and suffers from an inability to access, place, and then finally secure the nucleus replacement in place. Several attempts at human trials have even resulted in expulsion of these devices out of the disc space. This problem must be addressed to make this technology a viable possibility in spine treatment.

BRIEF SUMMARY OF THE INVENTION

There is disclosed systems and methods for spinal nucleus replacement by constructing channels through vertebral segments on either side of an area into which the spinal nucleus is to be positioned, the channels running from a channel end outside of the area to a channel end abutting the area. One end of a suture is inserted into the outside channel end of a first one of the channels and passed through the first channel and into the area and out of the area through the second channel until it emerges from the second channel. The suture is then used to pull the nucleus into the area.

In a first embodiment, an alignment device mounts to the posterior aspect of the spine and drills curved holes down through the pedicle of the segment and into the disc space of the level. At the adjoining level, holes are also drilled in the pedicle into the adjoining disc space so that each exit of the curved hole meet at a single disc space. A suture is then threaded through the first curved hole, to the disc space, then is extracted from the disc space to the posterior. The suture is threaded through a nucleus replacement, or through the covering around a nucleus replacement, and then back into the disc space where it is pulled through the second hole and out to the pedicle. Having a suture that goes through each pedicle and around the nucleus replacement allows the suture to be pulled from both ends to urge the nucleus replacement into position still secured to the suture. Plugs are then inserted into the pedicle and attached to the suture so as to fix the suture in place. The suture is then cut keeping the nucleus replacement in a fixed position within the disc space. The suture holds the nucleus replacement secured to a fixed position after it has been guided into place. While the nucleus replacement may be permitted a certain amount of movement in certain embodiments, it is secured within the disc space so as not to be expelled therefrom.

In a second embodiment, the ends of the suture expelled from both pedicles are joined with a tension band between the two pedicles that can act as a further stabilizing effect to the segment.

In a third embodiment, the pedicles of the same vertebra are used as access into the adjacent disc space. The two sutures or pathways are through the superior vertebral end place of the vertebra. This allows preservation of the entire periphery of the annulus fibrosis if the nucleus replacement is collapsible and can be inserted through the pedicle.

The foregoing has outlined rather broadly the features and technical advantages of the present invention in order that the detailed description of the invention that follows may be better understood. Additional features and advantages of the invention will be described hereinafter. It should be appreciated that the conception and specific embodiments disclosed may be readily utilized as a basis for modifying or designing other structures for carrying out the same purposes of the present invention. It should also be realized that such equivalent constructions do not depart from the invention. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
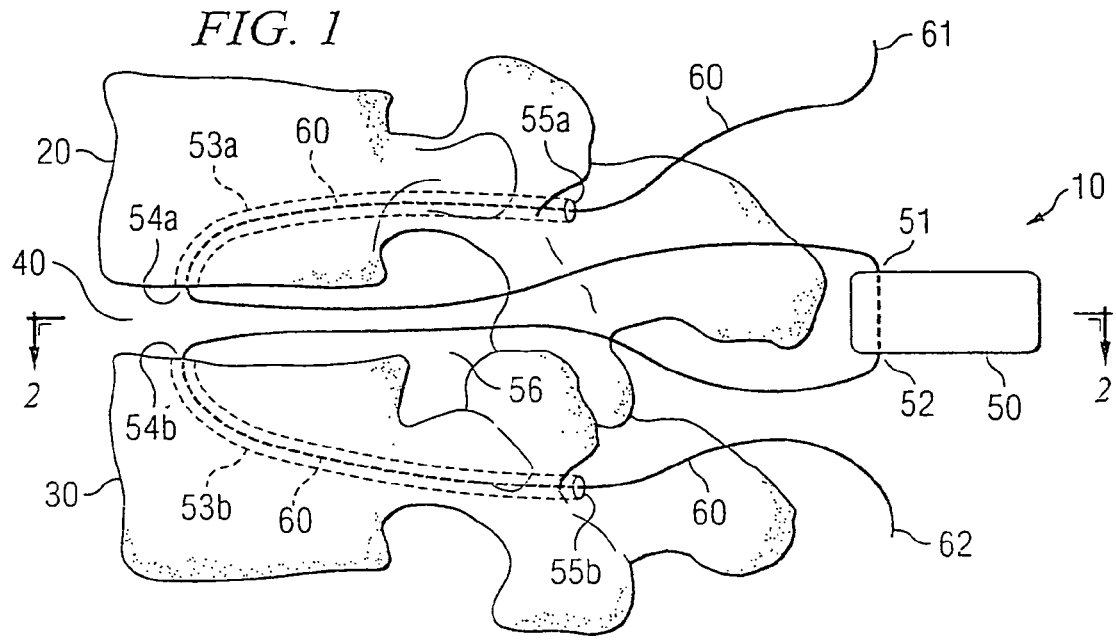
FIG. 1 shows a side view of the first embodiment.

Turning now to FIG. 1, vertebral segment 10 includes superior vertebral level 20 and inferior vertebral level 30. These are shown as level L4 and level L5 in this example, however the concepts taught herein could be used at any level in the spine. A description of a first embodiment of a device and method for using the device for inserting and securing a replacement nucleus within a disc space is now described in connection with vertabral segment 10 of FIG. 1. FIG. 1 shows a nucleus replacement 50 which must be inserted into the disc space 40. To assist this endeavor, two holes 53a and 53b are drilled into the vertebral levels 64, 65 using fluoro to track a cutting bit in its path, starting from the opening of the pedicles 55a, 55b and extending on a curved path to the disc space 40 as shown.

After the holes are drilled, a suture 60 starting with end 62 is passed through the L4 pedicle opening 55a, through the first tunnel 53a, and into the disc space 40 passing the entry point 54a. In the first embodiment, the suture would then be grasped and pulled through a posterior opening in the disc space 40, and out to the posterior of the patient. Suture 60 is then mated to nucleus replacement 50, and suture 60 is passed back down the access port to the disc space 40 where it is guided back down to the second tunnel 53b through opening 54b. As an aide, a tool could be passed through the opening of pedicle 55b, through tunnel 53b, into the disc space 40. The tool would grab suture 60 and pull end 62 through opening 54b, through tunnel 53b, and out to pedicle opening 55b where it is pulled out of the body.

This method leaves end 62 of suture 60 extending out of the patient and the opposite end 61 of suture 60 also extending out of the patient. The suture would most likely have been cut off at the appropriate length. Suture ends 61, 62 are then pulled out away from the patent, pulling with it nucleus prosthesis 50 that is attached to suture 60. In this way, nucleus replacement 50 is pulled into disc space 40 so that holes 54a, 54b are directly in line with the suture connection point at the nucleus prosthesis.

At this point knots, anchors (not shown) or other stop devices could be attached to suture ends 61, 62. If anchors are used, they would be forcibly press fitted or threaded into the pedicle. The anchors could have features on them that mate with the suture to allow tension and reduction of length on suture ends 61, 62 in a zip tie approach so as to maintain position of suture 60 and thus of nucleus replacement 50 at all times. The remaining suture ends would then be cut off flush or above flush to the anchors.

In another embodiment, end 62 of suture 60, while being installed, would pass from opening 54a of disc space 40 directly into opening 54b and urged through tunnel 53b to opening 55b of the L5 pedicle and pulled out of the patient. With end 62 of suture 60 extending out of the patient, a tool could be inserted through opening 56 to disc space 40, grabbing the suture 60 and pulling slack granted at either end through opening 56 and out of the patient. At this point, nucleus 50 would be harnessed to suture 60 at points 51 and 52. In so doing, nucleus replacement 50 is now secured to suture 60. Slack from suture 60 can now be pulled out by suture ends 61, 62, thereby pulling nucleus replacement 50 into disc space 40, with points 51, 52 positioned in line with openings 54a, 54b. Anchors would then be applied in the manner and fashion described above.

Figure 2:
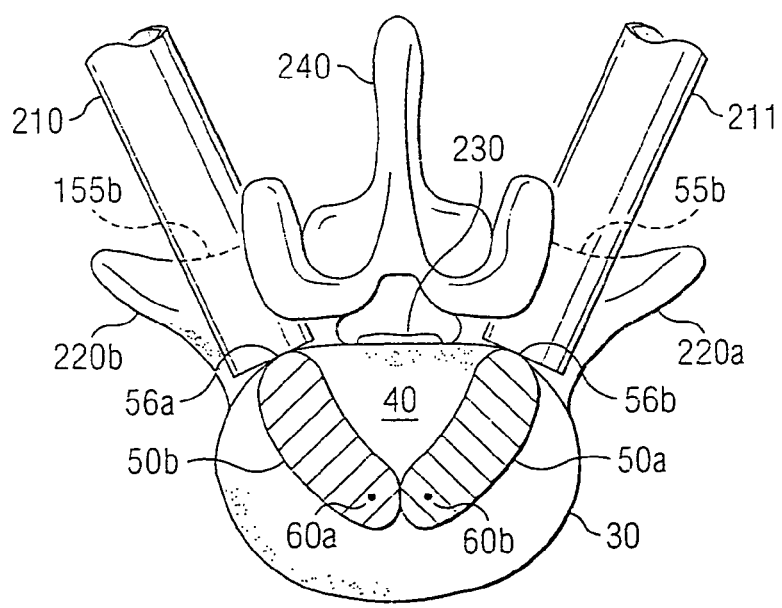
FIG. 2 shows a section view taken through line 2-2 of FIG. 1.

While in some instances nucleus replacement 50 may be a single device, in other implementations it may include multiple devices that are inserted into disc space 40. Turning to FIG. 2, a cross-section of the vertebral segment taken at line 2-2 of FIG. 1 is shown including vertebra 30 or L5 having spinus process 240, transverse processes 220a, 220b, and pedicle openings 55b, 155b which have been created by the method described above. The example of FIG. 2 shows an implementation in which two nucleus replacement devices (50a and 50b) have been inserted into disc space 40. For example, nucleus replacement 50a is inserted in the manner described above in connection with FIG. 1 for nucleus replacement 50, and nucleus replacement 50b is inserted in a similar manner. Cannulas 210, 211 are placed over the openings 55b, 155b to pass nucleus replacements 50a, 50b into the disc space 40. Suture 60 is shown coming out of the page at points 60a, 60b through attachment points 52a, 52b (not shown). The posterior longitudinal ligament (PLL) 230 is also shown in this view as being saved, making this method desirable for vertebral stability as the PLL 230 supplies mach of the posterior stability.

As a method, the nucleus replacements 50a, 50b are passed through cannulas 210, 211, through opening 56a, 56b of the disc space, and passed into the disc space 40. The nucleus replacement travel ends when holes 51a, 51b, and 52a, 52b (not shown), line up with holes 54a, 54b and 64a, 64b (not shown) with suture 60a passing though the left prosthesis 50a, and suture 60b passing through the right prosthesis 50b.

Figure 3:
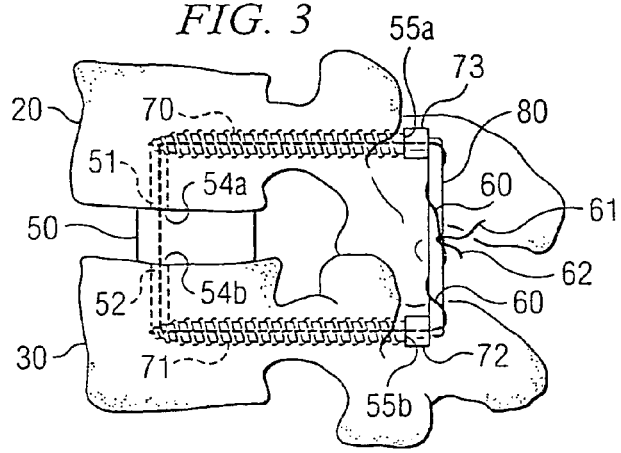
FIG. 3 shows a side view of the second embodiment.

Turning to FIG. 3, anchors 70, 71 are shown entering into pedicle holes 55a and 55b. At the proximal end of anchors 70, 71 are suture 60 securing means 72, 73 from which suture 60 is expelled. In this unique embodiment, suture ends 61 and 62 are joined at the ends to an elastic tension member 80 serving as a ligament to the anchors to achieve distraction of the disc space and to promote healthy biomechanics throughout the segment. The nucleus replacement 50 is shown in position within the disc space.

Figure 4A:
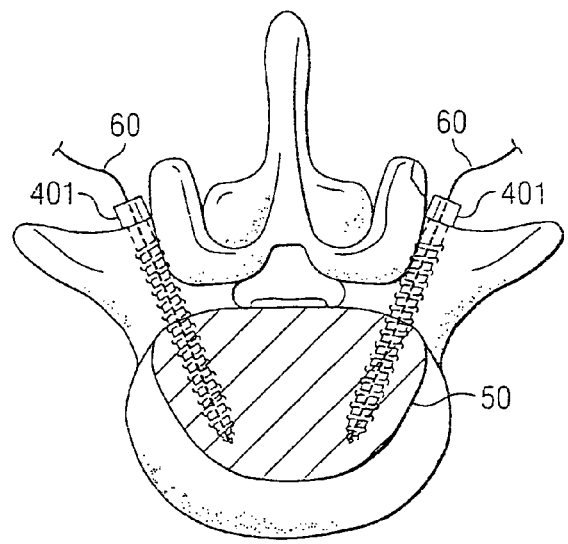
FIGS. 4A and 4B show a top view and a side view of the third embodiment.
Figure 4B:
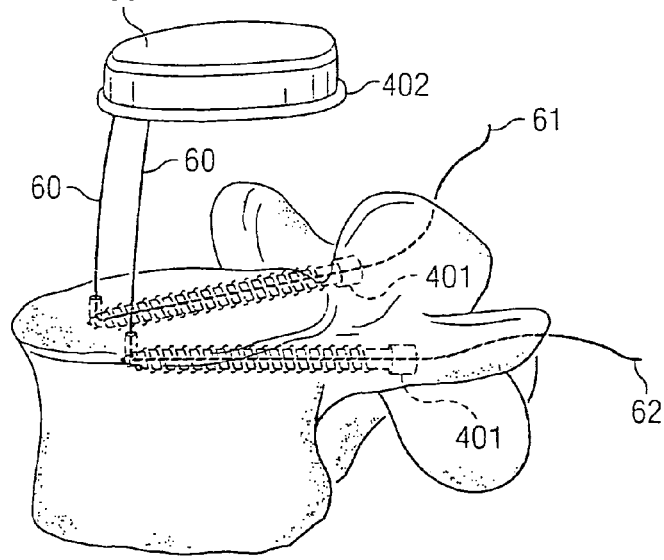

Turning to FIGS. 4A and 4B, a lower vertebra is shown in FIG. 4A with anchors 401 placed in the pedicles. The anchors allow for passage of suture through the pedicle to secure nucleus replacement 50 as described above. To assist with bone absorption and subsidence, as shown in FIG. 4B, nucleus replacement 50 could have a metal base 402 placed on one side to provide stability against the end plate. This metal base plate could be cobalt chrome or another biocompatible metal or it could be plastic, or rigid material. The nucleoplasty would be delivered in a translateral lumbar approach to the disc space. The anchors would be used to maintain position of the device and aid in insertion as described above.

Figure 5A:
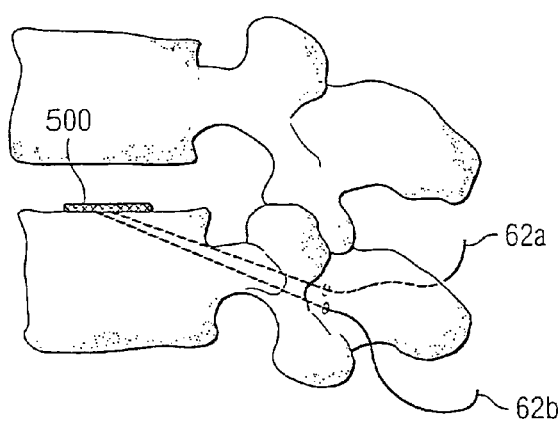
FIGS. 5A and 5B show top and side views of a vertebra having a collapsible reinforcement mesh.
Figure 5B:
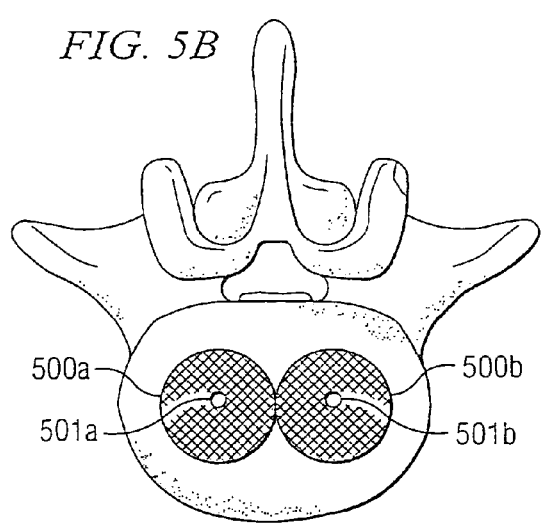

Turning to FIGS. 5A and 5B, a vertebral segment is shown including a cross section through the disc space of the lower vertebra. More specifically, FIG. 5A corresponds generally with the view of FIG. 1 and FIG. 5B corresponds generally with the view of FIG. 2. Also shown are a plurality of reinforcement mesh elements 500 (shown as elements 500A and 500B in FIG. 5B) which are collapsible under load. These mesh elements function to reinforce the end plate and the bone central to the end plate. That is, mesh elements 500 include a hole through which suture 60 is pulled, wherein mesh elements 500 reinforce the end plate and the bone central to the end plate to, for example, aid in preventing the hole in the underlying bone from growing larger over time due to stress presented thereto by the suture 60. This in turn allows for greater load bearing capability while avoiding bone absorption by the body as well as subsidence of an intervertebral implant. Suture ends 62A and 62B are shown in illustration (a), which are pulled through holes 501A and 501B of mesh elements 500A and 500B, respectively.

Figure 6A:
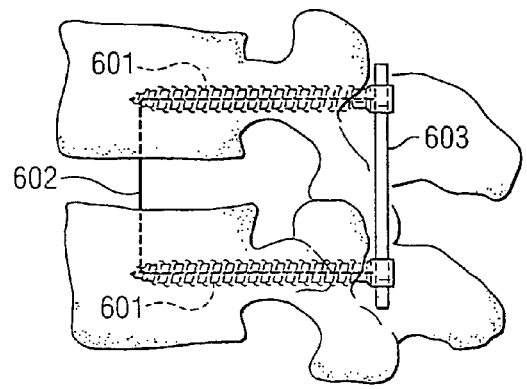
FIGS. 6A, 6B, and 6C show side views of a vertebral level having the invention implanted, the invention including a flexible rod which allows a supplemental rigid rod for salvage.
Figure 6B:
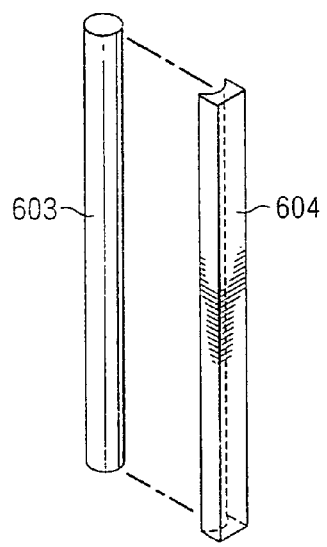
Figure 6C:
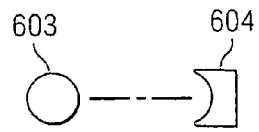

Turning to FIGS. 6A, 6B, and 6B, a side view of a vertebral segment is shown in FIG. 6A having pedicle anchors 601 which have a tension member 602 positioned at the distal end of the anchors. In this embodiment, a flexible rod 603 is secured to the anchors 601 between the segments to provide a dynamic stabilization system including the tension member in front and the counter tension member posterior. As shown in FIG. 6B, a salvage means including a supplemental rigid rod 604 which further secures to flexible rod 603 or anchors 601 can be used to allow for rigid fixation for fusion. One such fixation means of the supplemental rigid rod is shown in FIG. 6C which entails a piggy-back and interlock design. Rigid rod 604 includes a cylindrical cut that mates to flexible rod 603. It then locks to flexible rod 603 to make a conventional fusion.

Although the present invention and its advantages have been described in detail, it should be understood that various changes, substitutions and alterations can be made herein without departing from the invention. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the invention is intended to encompass within its scope such processes, machines, manufacture, compositions of matter, means, methods, or steps.

What is claimed is:

1. A method for spinal nucleus replacement, said method comprising:

removing a nucleus of an intervertebral disc;

drilling a first curved channel from an opening of a first pedicle through a first vertebra and into a nucleus area, drilling a second curved channel from an opening of a second pedicle through a second vertebra and into said nucleus area; said channels running from a channel end outside of said nucleus area to a channel end abutting said nucleus area;

inserting one end of a suture into said outside channel end of a first one of said channels and passing said suture end through said first channel and into said nucleus area;

inserting said suture end into the second of said channels and passing said suture end through said second channel until it emerges from said channel at said outside channel end of said second channel;

after insertion of said suture, attaching at least one load bearing nucleus replacement to a section of said suture between the ends of said suture, wherein said attaching occurs outside of said nucleus area; and pulling on at least one end of said suture to thereby pull said load bearing nucleus replacement into said nucleus area.

2. The method of claim 1 wherein said attaching occurs prior to said suture being pulled through said second channel.

3. The method of claim 1 further comprising:

connecting ends of said suture together outside of said nucleus area thereby holding said load bearing nucleus replacement within said nucleus area.

* * * * *